United States Patent
Rosengaus

(10) Patent No.: US 7,719,677 B2
(45) Date of Patent: May 18, 2010

(54) MULTI-SPECTRAL TECHNIQUES FOR DEFOCUS DETECTION

(75) Inventor: Eliezer Rosengaus, Palo Alto, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 230 days.

(21) Appl. No.: 12/069,997

(22) Filed: Feb. 14, 2008

(65) Prior Publication Data

US 2008/0212089 A1 Sep. 4, 2008

Related U.S. Application Data

(62) Division of application No. 11/227,720, filed on Sep. 15, 2005, now abandoned.

(60) Provisional application No. 60/707,440, filed on Aug. 11, 2005, provisional application No. 60/646,447, filed on Jan. 24, 2005.

(51) Int. Cl.
*G01J 3/00* (2006.01)
(52) U.S. Cl. ...................................................... 356/300
(58) Field of Classification Search .................. None
See application file for complete search history.

(56) References Cited

U.S. PATENT DOCUMENTS 5,943,126 A * 8/1999 Aloisio et al. ............. 356/237.1
6,922,236 B2 * 7/2005 Vaez-Iravani et al. ..... 356/237.2

* cited by examiner

*Primary Examiner*—Tu T Nguyen
(74) *Attorney, Agent, or Firm*—Deborah Wenocur

(57) ABSTRACT

A method and apparatus for improved defocus detection on wafers. The use of hyperspectral imaging provides increased sensitivity for local defocus defects, and the use of Fourier Space analysis provides increased sensitivity for extended defocus defects. A combination of the two provides improved overall sensitivity to local and extended defocus defects.

25 Claims, 6 Drawing Sheets

MULTI-SPECTRAL TECHNIQUES FOR DEFOCUS DETECTION

CROSS-REFERENCE TO RELATED APPLICATIONS

This application is a divisional of pending U.S. application Ser. No. 11/227,720, filed Sep. 15, 2005. The specification and drawings of 11/227,720 are hereby incorporated by reference.

This application is related to U.S. Provisional Application No. 60/646,447, filed Jan. 24, 2005, and to U.S. Provisional Application No. 60/707,440, filed Aug. 11, 2005, and claims priority from both.

FIELD OF THE INVENTION

This invention relates to integrated circuit processing, and in particular to detection of focus errors caused by the lithography stepper/scanner.

BACKGROUND OF THE INVENTION

As integrated circuits become smaller and faster, Critical Dimensions (CD's) of devices must decrease. Current state-of-the-art requires critical dimensions of approximately 0.1 micron, and manufacturers are striving to move to lateral dimensions of 65 nm. Consequently, better lithographic resolution is required in order to print smaller features. As per the Rayleigh limit, resolution r is inversely proportional to Numerical Aperture (NA) according to the equation $$r \propto \frac{\lambda}{NA},$$

where $\lambda$ is the wavelength of the radiation, for a diffraction-limited system. Therefore, to decrease (i.e., improve) resolution for a given wavelength of light, NA must be increased. Larger NA implies a larger collection angle of the lens, i.e., a collection angle of 180 degrees yields the maximum NA of 1. Present steppers have NA close to 1 to provide resolution of minimum size features.

A consequence of increased NA is a decrease in Depth of Focus (DOF), according to the equation $$DOF \propto \frac{\lambda}{(NA)^2}.$$

Current steppers therefore have decreased DOF due to improved resolution. This presents challenges in lithography, since out-of-focus exposure of features in photoresist smears the resist edges, as illustrated in FIG. 1. Incorrect lateral feature dimensions can result. If defocus is not detected, the microcircuit yields will suffer and the problem may not be detected until many steps later in the manufacturing process.

Steppers are generally equipped with autofocus, which tries to find the best focus for each field of the stepper (usually one die or several dies). However, several factors can cause local or global focus problems:

1) The mounting of the reticle, i.e., the master pattern, may have a tilt. This causes full-field focus problems.
2) The autofocus on the stepper may have a problem, which could cause a full-field defocus. Either of these problems would result in a defocus region of about one inch dimension.
3) Local deformation of the wafer, e.g., caused by contamination on the wafer backside or to structures on the frontside, can cause localized defocus, known as "hot spots". These may be 50-100 micron diameter.

One priority for Lithographic After-Development Inspection (ADI) is detection of focus errors in the stepper/scanner, so that corrective action can be taken immediately. Both localized and full-field defocus detection is needed. Traditionally, scanner/stepper defocus has been detected using manual inspection. One often-used detection method used in manual inspection of a wafer which has been patterned and has had the resist developed is to look for color changes across the wafer when observing the wafer under narrow-band diffuse illumination. Color changes result from out-of-focus regions, due to the fact that changing the profile of diffraction grating edges can drastically change its scattering profile and therefore can cause an apparent color change. This is seen from the grating equation:

$$\sin(\theta) - \sin(\theta_1) = n\lambda/D \quad (1),\text{ where}$$

$\theta$ = angle of observation with respect to normal
$\theta_1$ = angle of illumination with respect to normal
n = integer order
$\lambda$ = wavelength
D = grating pitch Since the repetitive structures on integrated circuits act as diffraction gratings, and since defocused regions have smeared edges as described above, defocused regions are evidenced by color changes. The operator cannot resolve the details of the patterning; he is merely detecting the collective diffractive effects of an area of patterned resist, i.e., "macro-inspection". From equation (1), it can be seen that variation of either angle or wavelength can affect the appearance of the grating.

The manual observation of color changes to detect defocused regions has severe limitations, due to the tri-stimulus color response of the eye, and its limited gray-scale depth at any wavelength. This is typically compensated for by mounting the wafer on a wobbler, and presenting it to the operator at a variety of angles. The human eye can thereby detect not only a slight color change, but also some "flashing" of the color change as the wafer rotates and wobbles. This method is the most effective for observing localized defocused regions.

Automated macro-inspection systems have also been used to detect defocus, along with other defects, using machine vision, i.e., imaging techniques. Such systems as the Nikon macro-inspection system uses a spin-wobble mount similar to that used in manual inspection, whereby the wafers are tilted and rotated around the azimuth. A high-resolution CCD camera images them through telecentric optics, and image processing is used to detect intensity variations in the observed image. The 2401 and 2430 inspection systems made by KLA-Tencor use narrow-spectral-band and broad-spectral band illumination, use monochrome sensors and detect defocus as an intensity change, and use a line-scan mechanism for imaging.

It is expected that existing automated macro-inspection systems will find it progressively more and more difficult to detect defocus as the CD's shrink, because visible wavelengths are being used, and the diffraction gratings created by the photoresist will have a pitch much smaller than the wavelength of the light used. Shorter wavelength light may damage the photoresist. The development of new methods with increased sensitivity for defocus detection, both for localized and extended defocus defects, will be important as critical dimensions continue to decrease.

SUMMARY OF THE INVENTION

It is therefore an object of this invention to provide an improved method and apparatus for defocus detection which does not employ a wobbler.

It is a further object of this invention to provide an improved method and apparatus for defocus detection which has lowered cost.

It is a further object of this invention to provide an improved method and apparatus for defocus detection which is more compact.

It is a further object of this invention to provide a method and apparatus for defocus detection which has increased sensitivity to extended defocus defects.

It is a further object of this invention to provide a method and apparatus for defocus detection which has increased sensitivity to defocus defects at smaller critical dimensions.

These objects are met in part by a method and associated apparatus for performing hyperspectral imaging to detect defocus.

These objects are further met in part by a method and associated apparatus for performing Fourier Space analysis.

DETAILED DESCRIPTION OF THE INVENTION

According to grating equation (1), it is clear that changes in the diffraction spectrum (generally observed as color changes) can be caused by varying either the angle or the wavelength of incident light. Whereas use of a wobbler enables observation of the effects of angle variation, the present invention utilizes, in one embodiment, variations in wavelength.

In a first embodiment of the invention, defocus is detected by accumulating information about the detected scattered and diffracted light in an image of a region of interest of a wafer, collected for several different discrete wavelengths or for a wavelength spectrum. The information collected is both spatial (i.e., image), and wavelength spectral. This technique when employed with high spectral finesse, is often referred to as "hyperspectral imaging".

A conventional monochromatic image is a function of the two spatial dimensions, $I(x,y)$, where $I$ is the intensity of the scattered and diffracted light from each point $(x,y)$. In hyperspectral imaging, additional information is collected by varying wavelength $\lambda$, to yield an intensity image $I(x,y,\lambda)$. In practice, the spectral information is typically not collected continuously, but rather at a number of discrete wavelengths. The spectral information can be derived in several ways:

a) Sequential illumination with or collection of narrow-band light.

A first sub-embodiment utilizes a series of filters selecting particular narrow wavelength bands from a broadband source, either during illumination or detection.

Figure 1A:
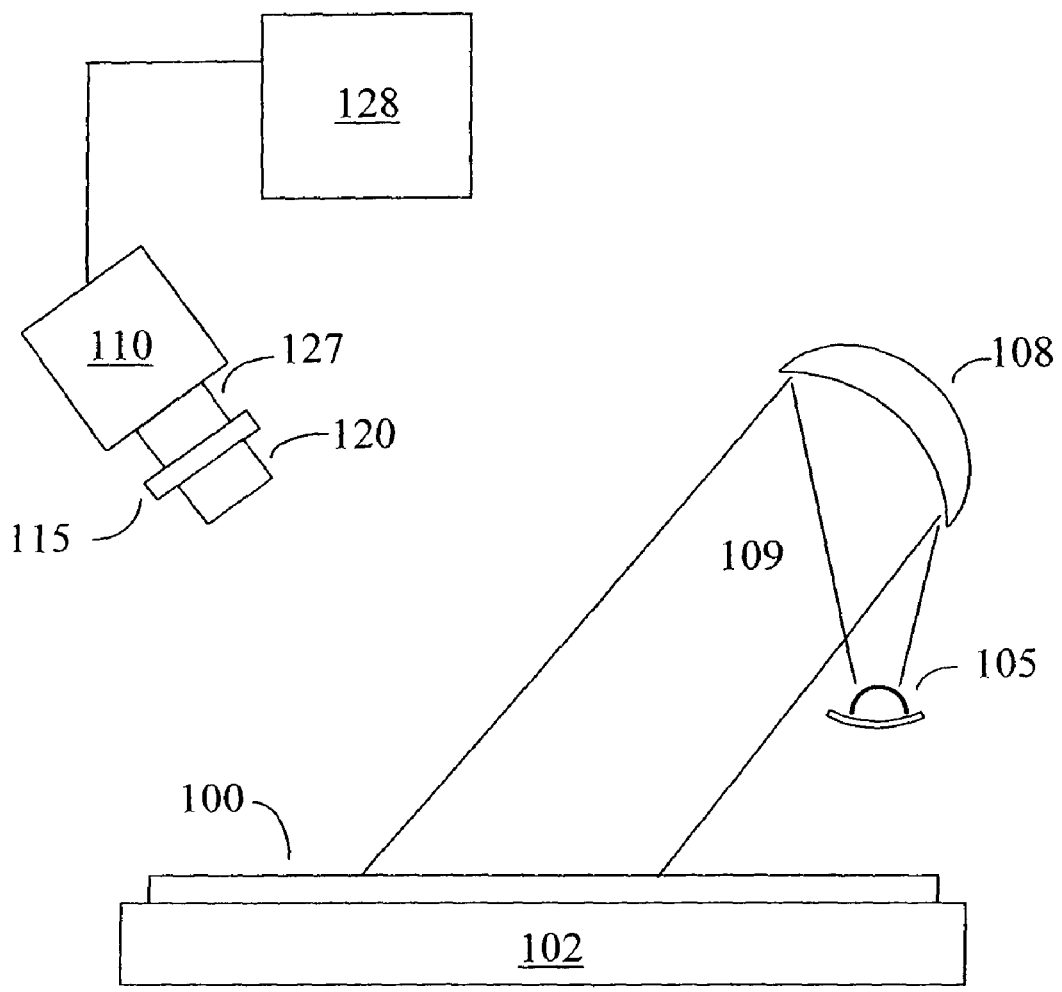
FIG. 1a illustrates an embodiment of the invention which employs a filter wheel comprising multiple optical narrow-band filters.

FIG. 1a illustrates one implementation of the first sub-embodiment which employs fixed absorption filters. Filter wheel 115 comprising multiple optical narrow-band filters is inserted between imaging lens 120 and camera 110. Relay 125 is between filter wheel 115 and camera 110. Wafer 100 on wafer holder 102 is illuminated by illuminator 105 which provides broadband light 109, such as a halogen incandescent bulb or other light source with black-body radiation characteristics. Mirror 108 may be used to collimate the light incident on the wafer. Camera 110 images the wafer using reflected, diffracted, or scattered light from the wafer surface. Computer 128 is optionally used for data analysis and control of parameters. An alternative implementation employs fixed interference filters in place of fixed absorption filters.

Figure 1B:
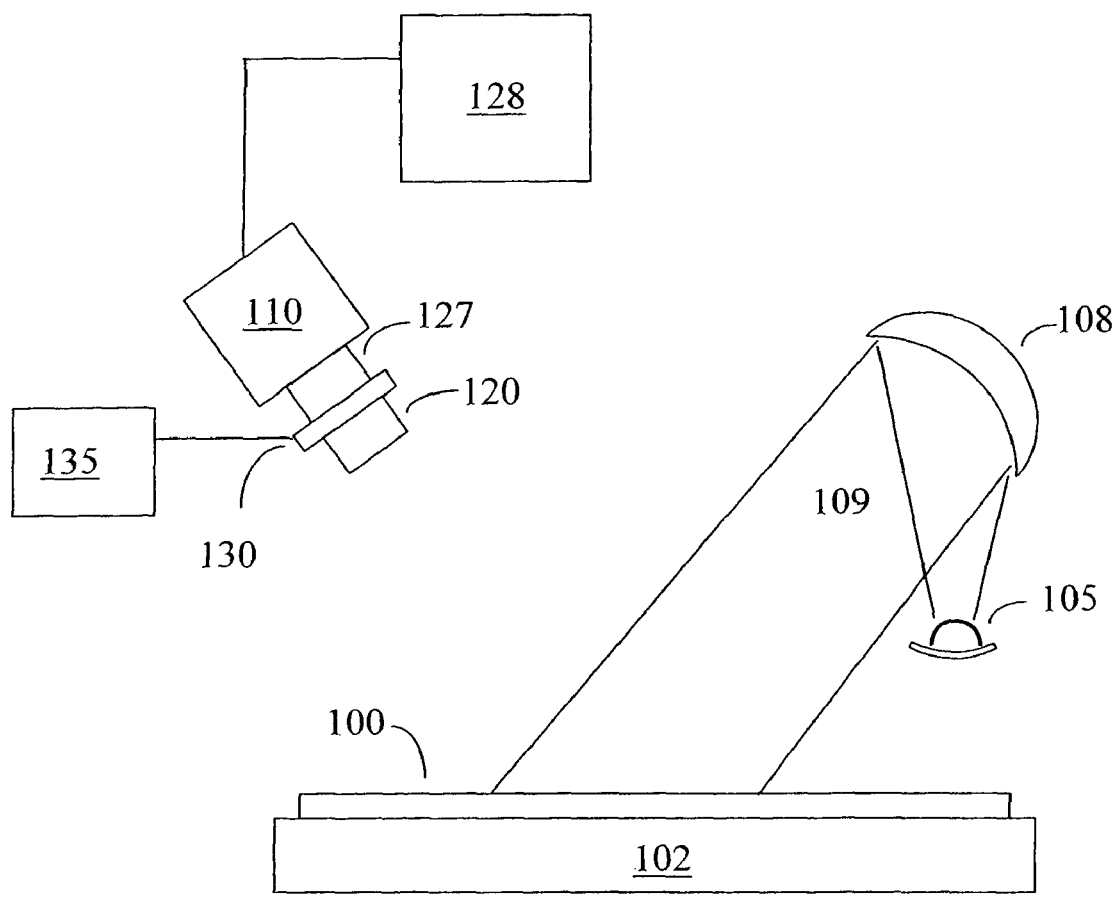
FIG. 1b illustrates an embodiment of the invention which employs a Liquid-crystal Fabry-Perot Etalon interferometer.

FIG. 1b illustrates a second implementation wherein Liquid-crystal Fabry-Perot Etalon interferometer 130 replaces filter wheel 115. Variable voltage supply 135 applies an adjustable electric field to the liquid crystals to modify their refractive index, whereby a continuously adjustable band-pass filter is implemented. An alternative implementation utilizes a bi-refringent Lyot filter in place of Fabry-Perot Etalon to provide continuously adjustable wavelength. Lyot filters are described in U.S. Pat. No. 5,809,048, issued Sep. 15, 1998.

A second sub-embodiment directly provides a series of different illumination wavelengths by illuminating with a collection of LED's of different wavelengths, rather than filtering broadband illumination.

b) Use of a dispersive element, (e.g., a prism or a diffraction grating) to angularly separate outgoing light of different wavelengths.

The spectral information can be obtained using a point-measuring system such as the Spectra CD system manufactured by KLA-Tencor, and spatial information would then need to be obtained using a scanning image-building method. Details of the Spectra CD system, including data analysis and signature matching to a database are described in U.S. Pat. No. 6,483,580, issued Nov. 19, 2002, which is hereby incorporated by reference. Alternately, imaging spectrometers such as the ST Mapper system manufactured by Filmetrics can be used to provide both the spatial and spectral information.

c) Use of an interferometer to either select the wavelengths for observation, or to spread the wavelengths in one dimension only. This method is generally referred to as Fourier Transform Spectroscopy, since the interference signal from the interferometer yields the Fourier Transform of the spectral intensity curve. The use of interferometers to form spectral images of a sample is described in U.S. Pat. No. 5,835,214, issued Nov. 10, 1998, the specification of which is hereby incorporated by reference. Many types of interferometers may by utilized, such as Fabry-Perot or Michaelson for wavelength selection, or Sagnac or generic "whiskbroom" or "pushbroom" interferometers for single dimension wavelength spreading. Use of a Sagnac interferometer is desirable for the present application due to its robustness and insensitivity to motion.

Figure 1C:
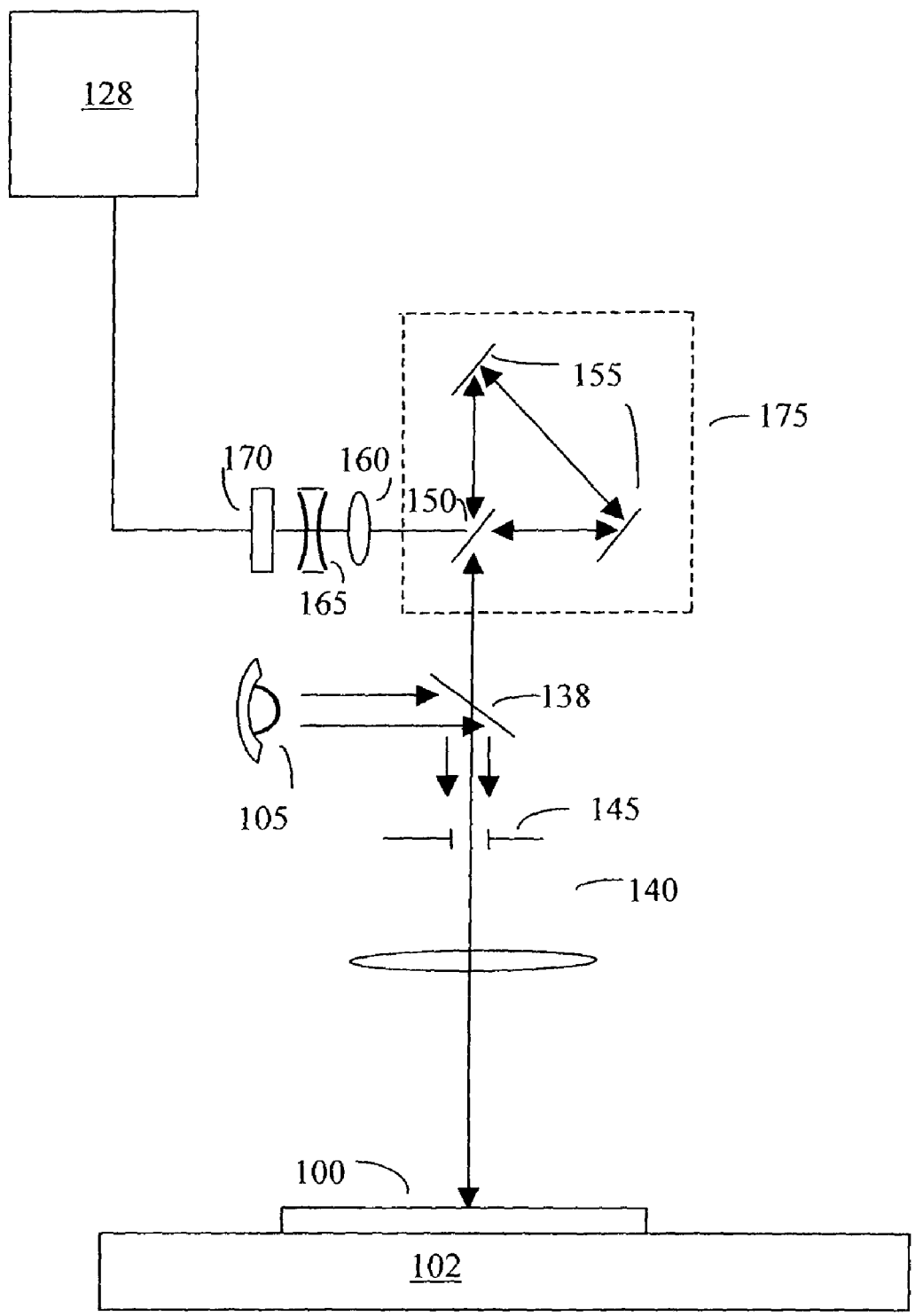
FIG. 1c illustrates an embodiment of the invention which employs a Sagnac interferometer.

FIG. 1c illustrates the implementation of a Fourier Transform spectrometer utilizing a Sagnac interferometer. Broadband illumination from illuminator 105 is incident (shown here as reflected by mirror 138 to provide normal incidence, though oblique incidence is also possible) on sample 100 mounted on xy stage 102. Image formation occurs by scanning the stage in one dimension. Outgoing light passes through lens 140 and aperture 145 into Sagnac interferometer 175. Beam splitter 150 sends light in two opposing directions to mirrors 155, then through Fourier transform lens 160, cylindrical lens 165, and to 2-D sensor array 170. Mirrors 155 are slightly tilted with respect to one another, making the two path lengths slightly different. Interference is observed between two close spots on the sample. Fourier transform lens 160 moves the infinity plane to a closer location, and cylindrical lens 165 undoes the Fourier transform in one dimension but preserves it in the other dimension. Data analysis for spatial and spectral image formation are performed by computer 128.

d) Utilizing imaging polarimetry to detect and observe defocus defects.

Spectroreflectometry can be further enhanced by collecting ellipsometric information $I(x,y,\lambda, P,P')$, where P is the polarization of the illuminating light, and P' is the polarization of the reflected light. An example of a system which might be used for this purpose is the KLA-Tencor Archer spectroscopic ellipsometer.

This method provides enhanced sensitivity to long features, particularly conducting features such as metal lines. Illumination for polarimetry is incident at an oblique angle, which will have a preferential direction related to long lines. Also, long conducting lines on the sample can act as a "polarization grating", and can short out electromagnetic radiation with electric field parallel to the conducting lines, even at normal incidence. Finally, oblique incidence illumination can also better isolate the top sample layer, since the surface is more reflective and mirror-like. In this embodiment, polarized light is incident upon the sample. Reflected light from the sample is analyzed to determine the effect the sample has had on the polarization of the light.

Figure 2:
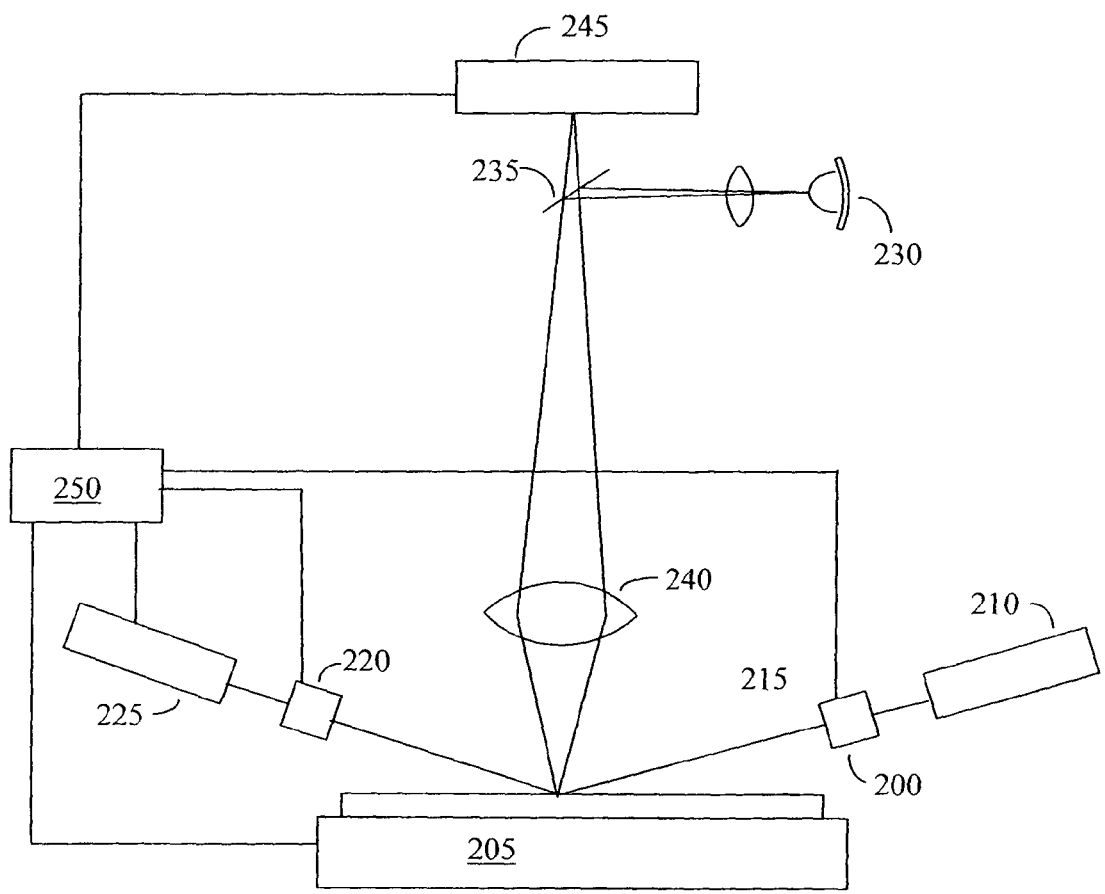
FIG. 2 illustrates an embodiment of the invention which employs a spectroscopic ellipsometer.

FIG. 2 illustrates a configuration whereby polarimetric information can be gathered in a point measurement spectroreflectometer. A more complete description is found in previously incorporated U.S. Pat. No. 6,483,580. Oblique incidence light from illuminator 210 passes through polarizer 215 to impinge on sample 200, which is mounted on xy stage 205. Outgoing light passes through analyzer 220 into spectrometer 225. Light from illuminator 230 passes through beamsplitter 235 and lens 240 to impinge at normal incidence onto sample 200. Reflected light is detected by spectroscopic reflectometer 245. Computer 250 performs data analysis, controls the travel of the xy stage to provide a scan and thereby build an image, and further controls other system parameters.

The addition of polarimetric information can enhance defocus detection, since without polarimetry, there may not be enough data available to distinguish between defocus and other process or material problems. Adding the extra parameter from polarimetry may provide sufficient data. However, the additional data necessitates more complicated mathematics and data analysis.

Using any of the above-described embodiments, multiple measurements are taken and images produced using different wavelength bands, or a continuous wavelength spectrum is obtained. Defocus may be detected by comparing the diffraction spectra and images of equivalent regions on different die, or by comparing the "defocus signature" of the area of interest with that of focus-exposure matrix wafers, which are commonly used for process monitoring. The comparison is a functional comparison, as opposed to a single value comparison, and can be accomplished in various ways, for example by using a $\chi^2$ test or similar functional comparison techniques such as comparison of spectrum statistics. The expected minimum number of different wavelength bands used for measurements is in the range of about 5 to 16 in order to detect a defocus signature, but may require larger numbers depending on the details of the pattern. The exact wavelengths and number of spectral bands can be determined at recipe setup time if focus-exposure matrices are used. A library or reference database of spectra from actual sample patterns may be built for comparison with in-use sample spectra, or alternatively a numerically simulated library of spectra may be built.

Data analysis, and computation of and comparison with library spectra, are generally performed by a computer which also may perform control functions such as wavelength variation. Data analysis for spectroscopic ellipsometry and spectroscopic scatterometry are described in previously incorporated U.S. Pat. No. 6,483,580.

In another embodiment of the invention, increased sensitivity to extended defocus defects is achieved using the principles of Fourier optics. The technique will be referred to hereinafter as "Fourier Space analysis". Prior imaging techniques as described above are sub-optimal, because spatial information is kept in the image, thereby making localization of the extended defects less exact. Defocus effects tend to be diffuse, so spatial pixel-by-pixel analysis is not optimally effective.

A basic principle of Fourier optics is that effects which are localized in physical space are diffuse in the Fourier domain, and that effects which are diffuse in physical space are localized in the Fourier domain. This phenomenon leads to the observation that transferring into Fourier space can enhance the detection and location of a diffuse effect such as diffuse defocus. The second embodiment of the present invention provides an optical Fourier transform, i.e., a Fourier Transform of the spatial image, to achieve the transference.

When an object is illuminated with a plane wave, i.e., coherent monochromatic light, the light that impinges on it will diffract and scatter in such a way that, at infinity (far-field), a pattern of light is seen which is the spatial Fourier transform of the object being illuminated. No refractive or reflective optics is necessary for this effect to occur. On the surface of the object, information is purely spatial. At infinity, it is purely frequency information, and in between it is a mixture of both. If the object has periodic structures thereon (such as for an integrated circuit wafer), the far-field pattern formed will contain some very intense "points" corresponding to the repetition frequency of the pattern. In particular, repetitive patterns which cover large areas on the object give rise to intense, angularly concentrated "pencils" of light; conversely, small, isolated objects in the spatial domain spread their energy angularly in a large number of directions, without forming any such pencils. Therefore, spatially diffuse effects such as field defocus result in high contrast pencils of light beams. One can observe defocus effects without resolving any of the structures that appear in the object. Repetitive small changes, such as resist profile changes, caused by defocus, can be seen in Fourier space as a significant change in the Fourier pattern. The far-field pattern can form relatively close to the object, e.g., several inches away from it, depending on the scale of the patterns on the object. Further propagation to "infinity" results in a better separation of the pencils of beams.

The present invention provides for the illumination of the wafer with coherent monochromatic illumination from a laser to cause the appearance of the Fourier transform at infinity, and further provides for the optional insertion of refractive or reflective optical components to move the far field pattern from infinity to a controlled finite position.

Figure 3:
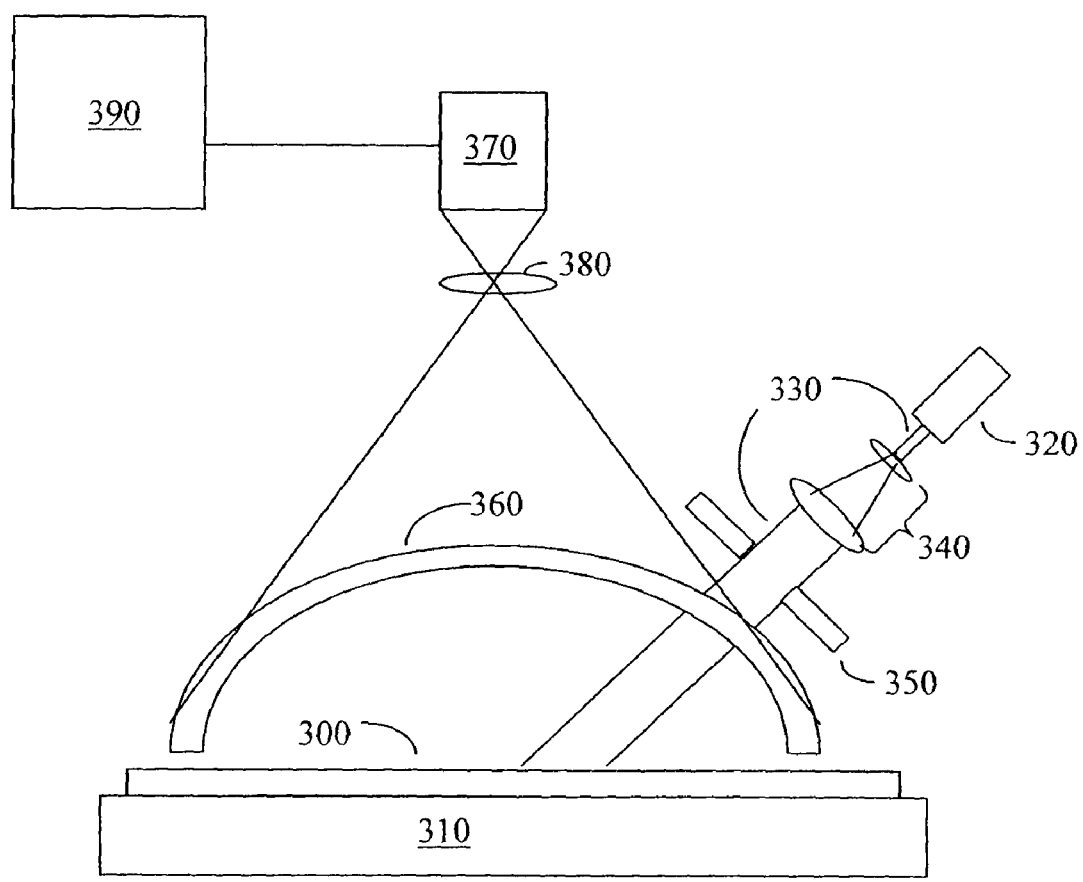
FIG. 3 illustrates an embodiment of the invention which utilizes Fourier Optics to detect extended defocus defects.

FIG. 3 illustrates this embodiment of the invention. Wafer 300 is mounted on x-y stage 310. Since the Fourier pattern is insensitive to positioning, the stage accuracy need not be very high. Laser 320 outputs laser beam 330 which is expanded by beam expander 340 and impinges on wafer 300 at an angle which is shown to be non-normal but may be modified to be normal incidence. Aperture or apertures 350 localize the beam to coincide with the sample field's boundary on the wafer. The far-field pattern is seen on screen 360 (which may be curved or hemispherical as shown, or may be flat) made of diffusing material such as Acrylite DF.

A conventional camera 370 and lens 380 image the screen and digitize the data. The camera used should have excellent dynamic range, which may be achieved by performing multiple exposures with progressively longer exposure times. This method will cause bright areas to saturate upon longer exposure, but dim areas will become more intense. This effectively increases the dynamic range of the camera, but requires good anti-blooming measures. Computer 390 is used for data analysis, as well as optionally for control of the process parameters.

Other optical components can be used in place of or in addition to the screen. For example, a large diameter lens could be used to directly capture the outgoing pencils of light and relay them to an image plane. Such lenses, being of large diameter, are expensive to manufacture, but a low-quality plastic lens may suffice and is much less costly than a high-quality lens. A second alternative is to use a large-size replicated mirror to relay the outgoing light to an image plane. Such mirrors are low-cost, but have long focal lengths, making the system large in size. Optical folding may mitigate this problem.

Each sample field generates one image, which contains a signature of the field. Extended defects are detected by comparing the images to other similar images. The image may be mostly dark, with the defect-relevant information being contained in a relatively small portion of the image.

Computer-implemented data analysis is utilized to extract defocus information from the Fourier Space analysis described above. The details of the algorithms used to flag large-scale defects depend on the structures being imaged. To a first approximation, a simple subtraction of the patterns followed by a thresholding step may be sufficient. In addition, spatial filtering can be done by ignoring certain areas of the acquired image. A library of Fourier signatures can be collected using standard focus-exposure matrix wafers, which are commonly used for process monitoring. This embodiment of the invention provides increased (relative to pixel-based imaging schemes) sensitivity to extended, i.e., large-area defects such as defocus, since it uses the complete Fourier spectrum, and because it utilizes data from a full exposure field.

Figure 4:
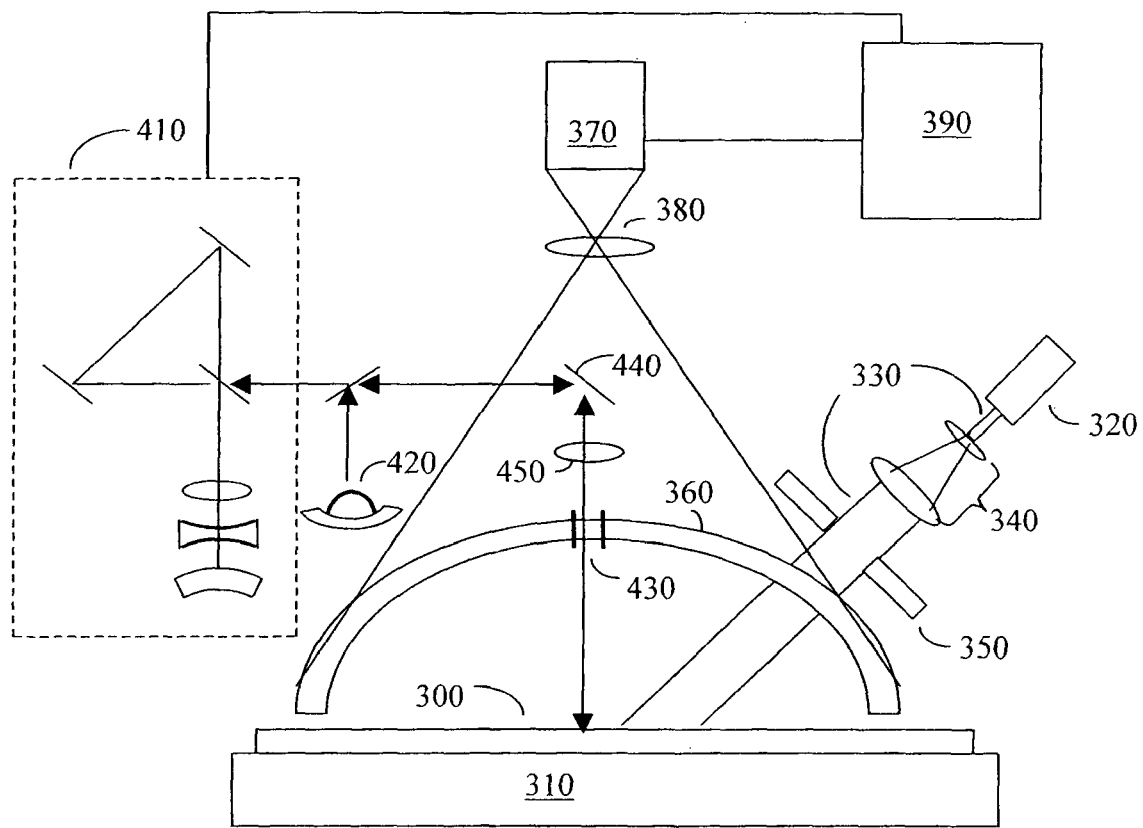
FIG. 4 illustrates an embodiment of the invention which combines hyperspectral analysis with Fourier imaging.

Another embodiment of the invention combines a plurality among the above-described embodiments to provide improved sensitivity to both localized and extended defocus defects. FIG. 4 shows one possible configuration for a sub-embodiment combining hyperspectral analysis using an imaging spectrometer with Fourier imaging of extended defocus defects. Aperture 430 in screen 360 enables normal incidence of broadband illumination from illuminator 420 onto sample 300. Mirror 440 deflects the light so that the imaging spectrometer does not impede the line of sight of camera 370 onto screen 360. Imaging spectrometer 420 is shown with Sagnac interferometer configuration, but could utilize other types of interferometers or other imaging spectrometers. A possible methodology would include Fourier space analysis for gross defect detection, followed by honing in on a few selected spots using a point measuring or imaging spectrometer.

The present invention provides a method and apparatus for improving the sensitivity of defocus detection, both for localized and for extended defects, by detecting and analyzing additional information about reflected, diffracted, and scattered light from the sample surface. This additional information may include spectral, polarization, or frequency data as well as spatial information. All of the embodiments can be integrated into present macro inspection systems.

In order to optimize defocus detection, special targets may be printed on each wafer on such unused real estate as inside the inter-die streets. The targets are designed to show defocus, such as a well controlled diffraction grating structure.

It is not intended that the present invention be limited to the exact embodiments described herein. It should be apparent to those skilled in the art that changes and modifications can be made without departing from the inventive concept. By way of example, any of the methods can be used for spot sampling in place of imaging, e.g. for determining full field defocus. Other types of varied wavelength illumination sources may be used, for example lasers, arc lamps, fluorescent sources, luminescent sources. Other interferometer types may be used. The scope of the invention should be construed in view of the claims.

With this in mind, I claim:

1. A method for detecting extended defocus defects on a sample surface comprising:
    illuminating said sample surface with coherent monochromatic light;
    observing a far-field intensity image of outgoing light from said sample surface which is the spatial Fourier transform of said sample surface;
    using a computer to compare said far-field intensity image with a reference far-field intensity image; and
    from said comparison, locating extended defocus defects on said sample surface.

2. The method of claim 1, wherein said step of observing a far-field intensity image of outgoing light from said sample surface which is the spatial Fourier transform of said sample surface comprises providing an imaging surface at a distance sufficiently far from said sample surface to see said far-field pattern thereon.

3. The method of claim 2, further including the step of imaging said imaging surface with a camera.

4. The method of claim 3, further including the step of digitizing the data obtained from said imaging and analyzing said digitized data using a computer.

5. The method of claim 4, wherein said step of analyzing said digitized data using a computer comprises a simple subtraction of patterns followed by a thresholding step.

6. The method of claim 2, further including the step of relaying said outgoing light to said imaging surface comprising an image plane.

7. The method of claim 6, wherein said step of relaying said outgoing light to said imaging surface comprising an image plane is performed using one selected from the group consisting of: directly capturing outgoing pencils of light with a large diameter lens, and using a large-size replicated mirror.

8. The method of claim 1, wherein said step of comparing said far-field intensity image with a reference far-field intensity image comprises:
  generating one image from a sample field, which contains a signature of the field; and
  comparing said image to other similar images from other similar fields.

9. The method of claim 1, wherein said reference far-field intensity image is a Fourier signature chosen from a library of Fourier signatures collected using focus-exposure matrix wafers.

10. An apparatus for detecting extended defocus defects on a sample surface comprising:
  a holder for holding a sample thereon;
  a coherent monochromatic light source arranged to illuminate said sample surface with coherent monochromatic light;
  an imaging surface positioned at a distance sufficiently far from said sample surface to observe thereon a far-field intensity image of outgoing light from said sample surface which is the spatial Fourier transform of said sample surface;
  an imager for imaging said imaging surface; and
  a computer for comparing said far-field intensity image with a reference far-field intensity image.

11. The apparatus of claim 10, wherein said sample holder includes an x-y stage.

12. The apparatus of claim 10, wherein said imager comprises a lens positioned to direct said outgoing light onto said imaging surface, and a camera.

13. The apparatus of claim 10, further including a relay for relaying said outgoing light to said imaging surface comprising an image plane.

14. The apparatus of claim 13, wherein said relay is one of the group consisting of: a large diameter lens for directly capturing outgoing pencils of light, and a large-size replicated mirror.

15. The apparatus of claim 10, further including an analyzer coupled to said imager for analyzing data.

16. The apparatus of claim 15, wherein said analyzer includes a computer.

17. The apparatus of claim 15, wherein said analyzer is configured to:
  generate an image from a sample field, which contains a signature of the far-field pattern of the field; and
  compare said image to other similar images from other similar fields.

18. The apparatus of claim 17, wherein said analyzer is further configured to compare said image to other similar images from other similar fields by a simple subtraction of patterns followed by a thresholding step.

19. A non-transitory computer-readable storage medium containing computer executable code to:
  generate an image from a sample field from a sample surface illuminated with monochromatic coherent light, said image containing a signature of the far-field pattern of the field; and
  compare said image to other similar images from other similar fields;
  by the steps of:
  illuminating said sample surface with coherent monochromatic light;
  observing a far-field intensity image of outgoing light from said sample surface which is the spatial Fourier transform of said sample surface;
  using a computer to compare said far-field intensity image with a reference far-field intensity image; and
  from said comparison, locating extended defocus defects on said sample surface.

20. A method for detecting local and extended defocus defects on a sample surface comprising:
  illuminating said sample surface with coherent monochromatic light;
  observing a far-field intensity image of outgoing light from said sample surface which is the spatial Fourier transform of said sample surface;
  using a computer to compare said far-field intensity image with a reference far-field intensity image;
    further using a spectroreflectometric technique to form an intensity image of outgoing light from a portion of said sample surface, $I(x,y,\lambda)$ including a plurality of wavelengths $\lambda$;
  comparing said intensity image with a reference intensity image; and
  from said comparisons, locating both local and extended defocus defects on said sample surface.

21. The method of claim 20, wherein said steps of:
  illuminating said sample surface with coherent monochromatic light;
  observing a far-field intensity image of outgoing light from said sample surface which is the spatial Fourier transform of said sample surface; and
  comparing said far-field intensity image with a reference far-field intensity image;
  are performed for gross defect detection; and
  wherein said steps of:
    further using a spectroreflectometric technique to form an intensity image of outgoing light from a portion of said sample surface, $I(x,y,\lambda)$ including a plurality of wavelengths $\lambda$;
  comparing said intensity image with a reference intensity image
  are performed on selected spots on said sample surface for detailed defect detection.

22. The method of claim 20, wherein said spectroreflectometric technique is selected from the group consisting of:
  a) sequentially illuminating said sample surface with narrow-band light having a plurality of wavelengths, and analyzing outgoing light from said sample surface;
  b) illuminating said sample surface with broadband light, then selecting a plurality of narrow wavelength bands of outgoing light for detection and analysis using at least one band pass filter;
  c) illuminating said sample surface with broadband light, then angularly separating light of different wavelengths outgoing from said sample surface using a dispersive element, and analyzing said light outgoing from said sample surface; and
  d) illuminating said sample surface with broadband light, then using an interferometer for one of the group consisting of: selecting the wavelengths of outgoing light from said sample surface for observation, and spreading said wavelengths of outgoing light from said sample surface in one dimension only.

23. An apparatus for detecting local and extended defocus defects on a sample surface comprising:
  a sample holder for holding a sample to be illuminated;
  an illuminator arranged to provide a first incident light onto said sample;
  a detector for detecting outgoing light from said illuminated sample surface;
  a hyperspectral imager arranged to form an intensity image $I(x, y, \lambda)$ of first outgoing light from said illuminated sample surface;

an analyzer configured to compare said intensity image to a reference intensity image;

a coherent monochromatic light source arranged to illuminate said sample surface with a second incident light, said second incident light being coherent monochromatic light;

an imaging surface positioned at a distance sufficiently far from said sample surface to observe thereon a far-field intensity image of outgoing light from said sample surface which is the spatial Fourier transform of said sample surface;

a far field imager for imaging said imaging surface; and a computer for comparing said far-field intensity image with a reference far-field intensity image.

24. The apparatus of claim 23, wherein:
said illuminator is a broadband illuminator;
said imaging surface is a screen having an aperture therethrough to admit said first incident light onto said sample surface.

25. The apparatus of claim 24, wherein said hyperspectral imager is an imaging spectrometer, and further including a mirror positioned to deflect said first outgoing light such that said imaging spectrometer does not impede line of sight of said far field imager onto said imaging surface.

* * * * *